(12) United States Patent
Cummings

(10) Patent No.: US 8,087,287 B2
(45) Date of Patent: Jan. 3, 2012

(54) METHOD FOR ANALYZING ENGINE OIL DEGRADATION

(75) Inventor: Jill M. Cummings, Bay City, MI (US)

(73) Assignee: GM Global Technology Operations LLC, Detroit, MI (US)

( * ) Notice: Subject to any disclaimer, the term of this patent is extended or adjusted under 35 U.S.C. 154(b) by 524 days.

(21) Appl. No.: 12/268,666

(22) Filed: Nov. 11, 2008

(65) Prior Publication Data

US 2010/0116022 A1    May 13, 2010

(51) Int. Cl.
G01N 33/26  (2006.01)
G01N 1/44  (2006.01)
(52) U.S. Cl. .............. 73/53.05; 73/23.37; 73/23.38; 73/23.41; 436/60
(58) Field of Classification Search ............ 73/23.37, 73/23.38, 23.41, 53.05, 61.52, 61.55, 61.58; 436/60
See application file for complete search history.

(56) References Cited

U.S. PATENT DOCUMENTS

| | | | | |
|---|---|---|---|---|
| 4,298,472 | A * | 11/1981 | Durand et al. ............ | 210/198.2 |
| 4,493,765 | A * | 1/1985 | Long et al. ................ | 208/309 |
| 4,764,258 | A * | 8/1988 | Kauffman ................. | 205/786 |
| 5,071,527 | A * | 12/1991 | Kauffman ................. | 205/786 |
| 5,354,475 | A * | 10/1994 | Bakker ..................... | 210/656 |
| 6,217,745 | B1 * | 4/2001 | Fang ......................... | 205/775 |
| 6,225,061 | B1 | 5/2001 | Becker et al. | |
| 6,327,900 | B1 | 12/2001 | Mc Donald et al. | |
| 6,464,859 | B1 * | 10/2002 | Duncum et al. .......... | 208/263 |
| 6,497,138 | B1 | 12/2002 | Abdel-Rahman et al. | |
| 2004/0118744 | A1 * | 6/2004 | Daniel et al. ............. | 208/18 |
| 2005/0167337 | A1 * | 8/2005 | Bunger et al. ............ | 208/254 R |
| 2009/0184030 | A1 * | 7/2009 | Yen et al. ................. | 208/180 |

FOREIGN PATENT DOCUMENTS

| | | |
|---|---|---|
| CN | 101825616 | 9/2010 |
| DE | 102009052006 | 7/2010 |

OTHER PUBLICATIONS

Sepcic, Kelly, et al., "Diagnosis of used engine oil based on gas phase analysis," The Analyst, vol. 129, pp. 1070-1075 (2004) (first published online Aug. 26, 2004).

Environmental Protection Agency, Test Methods for Evaluating Solid Waste, Physical/Chemical Methods—SW-846—Method 8260B (Revision 2) entitled "Volatile Organic Compounds by Gas Chromatography/Mass Spectrometry (GC/MS)" (Dec. 1996).

ASTM Standard D6971-04, "Standard Test Method for Measurement of Hindered Phenolic and Aromatic Amine Antioxidant Content in Non-zinc Turbine Oils by Linear Sweep Voltammetry," ASTM International, DOI: 10.1520/D6971-04, http://www.astm.org/Database.Cart/Historical/D6971-04.htm (2004) (summary only).

\* cited by examiner

*Primary Examiner* — Daniel Larkin
(74) *Attorney, Agent, or Firm* — Harness, Dickey & Pierce, P.L.C.

(57) ABSTRACT

The present disclosure provides a method for detecting degradation of an engine oil, by separation into a polar component and a non-polar component via admixture with a polar solvent having a polarity index greater than or equal to 5 and optionally a non-polar solvent having a polarity index of less than or equal to about 1. The polar component is analyzed for one or more degradation indicators selected from the group consisting of antioxidants, acid content, and combinations thereof. Such degradation indicators relate to a degree of engine oil degradation. The polar component may be analyzed by Gas Chromatography and Mass Spectrometry (GC/MS) for the one or more degradation indicators, which can provide a semi-quantitative level of such degradation indicator species. The non-polar component identifies combustion products that help to explain the level of degradation.

22 Claims, 1 Drawing Sheet

US 8,087,287 B2

METHOD FOR ANALYZING ENGINE OIL DEGRADATION

FIELD

Figure 1A:
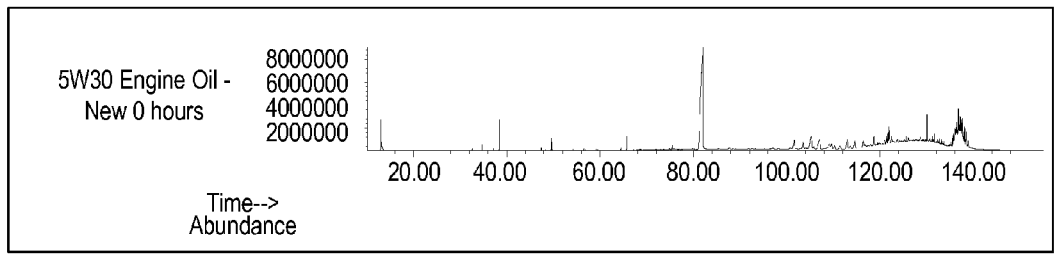
Figure 1B:
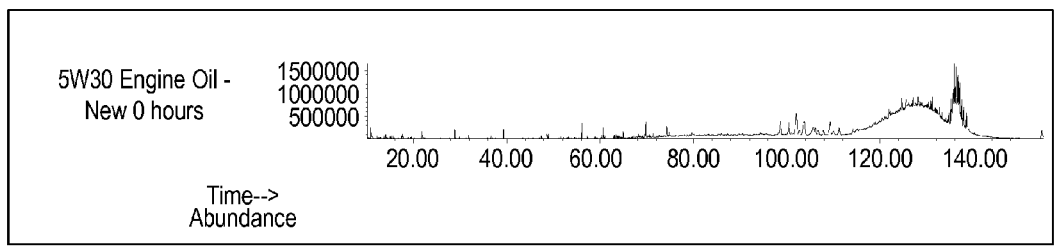
Figure 1C:
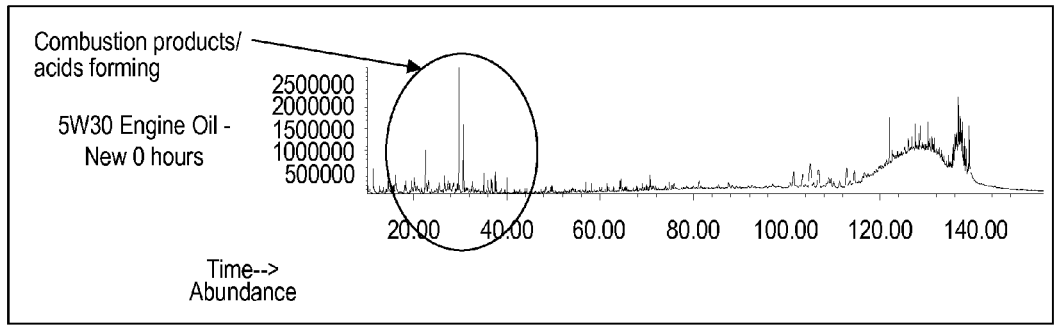

The present disclosure relates to a method for analyzing engine oil, and more particularly to a method for determining a level of degradation of engine oil used in an internal combustion engine.

BACKGROUND

This section provides background information related to the present disclosure which is not necessarily prior art.

When engine oil for an internal combustion engine loses its lubricating properties, an oil change is required. The loss of adequate lubrication exposes an engine to potential wear, damage, and durability issues. The life of the oil is directly related to the amount of oxidation, contamination, and physical wear to which it is exposed. Antioxidants, present to prevent oil oxidation and ultimately degradation, become inactive at high engine temperatures, or with exposure to moisture thus the engine oil potentially loses its lubricating properties which can affect the efficiency of the engine vehicle fuel economy, and prematurely wear engine components. As the engine oil becomes more viscous and acidic due to oxidation and nitration, insoluble materials such as varnish and sludge may be deposited on the engine surfaces.

Engine design and oil durability can be optimized to decrease engine wear and increase engine oil life. By measuring the rate at which oxidation and contamination are degrading the oil, a determination can be made regarding the remaining life of the engine oil and how well the engine oil is protecting the engine. The increases in degradation by-products levels and decreases in antioxidant content accelerate the breakdown of the oil. The oxidation reactions initiate more reactions and then propagate to the point where the engine oil may potentially become corrosive to the engine and cause damage to components or complete failure, if it is not replaced with new oil.

It is desirable to detect which engine oils, engines, and operating conditions reduce or eliminate wear, increase durability, or present a risk for engine failure. Current tests do not measure both decreased antioxidant content and increases in degradation by-products and fuel combustion products within engine oil.

SUMMARY

In various aspects, the present disclosure provides a method for detecting degradation of an engine oil. In certain aspects, the method comprises separating an engine oil sample into a polar component and a non-polar component. The polar component is analyzed for one or more degradation indicators selected from the group consisting of antioxidants, acid content, and combinations thereof. Such degradation indicators relate to a degree of engine oil degradation. The method comprises extracting the polar component with a polar solvent. In certain aspects, the polar solvent has a polarity index of greater than or equal to five. The polar solvent can be an alkanol having one to four carbon atoms. In certain aspects, the polar solvent comprises methanol. In certain aspects, the method comprises extracting the non-polar component with a non-polar solvent. In certain aspects, the non-polar solvent has a polarity index of less than or equal to one, optionally less than or equal to about 0.5, and in certain aspects of about 0.1. In certain aspects, the non-polar solvent is an alkane having six to nine carbon atoms. In certain aspects, the non-polar solvent comprises heptane. In certain aspects, the engine oil sample is admixed with the polar solvent to form a mixture (e.g., solution), which is then agitated and permitted to settle for at least twenty-four hours. In certain aspects, the method comprises analyzing the polar component by gas chromatography and mass spectrometry (GC/MS).

In certain aspects, the present disclosure pertains to a method for detecting engine oil degradation comprising determining a first amount of one or more degradation indicators selected from the group consisting of antioxidants, acid content, and combinations thereof in a first engine oil composition. The first engine oil composition is separated into a polar component and a non-polar component. The polar component is then analyzed, so that the first amount of the one or more degradation indicators relates to a degree of degradation of the first engine oil composition. The non-polar component is optionally analyzed for hydrocarbon combustion by-products. The method further comprises determining a second amount of one or more degradation indicators selected from the group consisting of antioxidants, acid content, and combinations thereof in a second engine oil composition that is distinct from the first engine oil composition. The second engine oil composition is separated into a polar component and a non-polar component, where the polar component is then analyzed. Again, the second amount of the one or more degradation indicators relates to a degree of degradation of the second engine oil composition. In this regard, the first amount of the one or more degradation indicators can be compared to the second amount of the one or more degradation indicators to determine the relative engine oil degradation of the first oil composition as compared to the second oil composition. In certain aspects, the method includes determining a semi-quantitative difference between the first degradation indicator species and the second degradation indictor species, for example, by semi-quantitative analysis of mass spectrometry results after gas chromatography processing by way of comparison of the integrated area of the processed peaks.

In yet other aspects, the present disclosure provides a method for detecting degradation of an engine oil comprising admixing an engine oil sample with a polar solvent to form a mixture. The mixture is then agitated and permitted to separate for at least twenty-four hours to form a polar component and a non-polar component. The polar solvent optionally comprises an alkanol. In certain aspects, the polar component is analyzed by gas chromatography/mass spectrometry (GC/MS) to determine a presence of one or more degradation indicator species selected from the group consisting of antioxidants, acid content, and combinations thereof, where such degradation indicator species relate to a degree of engine oil degradation.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Figure 1D:
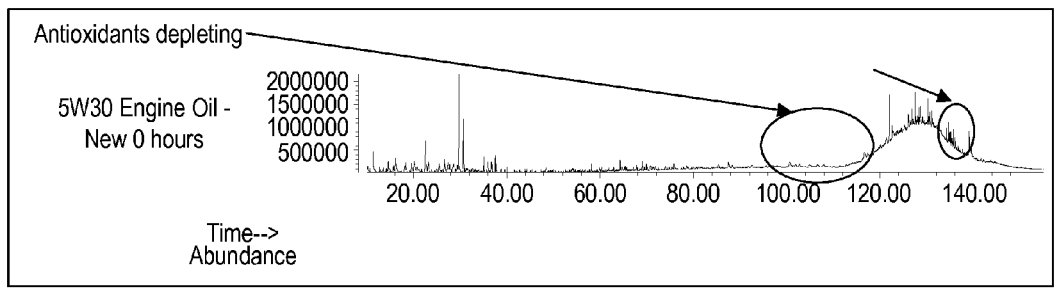

FIGS. 1A-D show gas chromatography (total ion chromatographs) of an exemplary engine oil (commercially available as a 5W30) tested for degradation indicator species prior to use in an internal combustion engine (0 hours) (FIG. 1A), at 30 hours of use (FIG. 1B), at 411 hours of use (FIG. 1C), and at 490 hours of use (FIG. 1D).

Corresponding reference numerals indicate corresponding parts throughout the several views of the drawings.

DETAILED DESCRIPTION

Example embodiments will now be described more fully with reference to the accompanying drawings.

The present disclosure provides a method for detecting engine oil degradation by separating an engine oil sample into a polar component and non-polar component. The polar component is then analyzed for one or more degradation indicator species selected from the group consisting of antioxidants, acid content, and combinations thereof, which respectively relate to a degree of engine oil degradation.

Antioxidants are added to engine oil for internal combustion engines, generally as an antioxidant package to prolong engine oil life. As engine oil physically wears and chemically ages, the antioxidant content will decrease. The base oil transforms into degradation by-products, reducing the capability of the engine oil to protect the engine. By way of example, conventional engine oil bases can be derived from natural lubricating oils, synthetic lubricating oils, or combinations thereof. Suitable engine oil base include bases obtained by isomerization of synthetic wax and slack wax, as well as hydrocrackate basestocks produced by hydrocracking (rather than solvent extracting) the aromatic and polar components of the crude. Engine oils include petroleum oils, mineral oils, and oils derived from coal or shale which are refined by typical procedures including fractionating distillation, solvent extraction, dewaxing and hydrofinishing.

Synthetic oils include hydrocarbon oils and halo-substituted hydrocarbon oils such as polymerized and interpolymerized olefins, alkylbenzenes, polyphenyls, alkylated diphenyl ethers, alkylated diphenyl ethers, alkylated diphenyl sulfides, as well as their derivatives, analogs, and homologs thereof, and the like. Synthetic engine oils also include alkylene oxide polymers, interpolymers, copolymers and derivatives thereof wherein the terminal hydroxyl groups have been modified by esterification, etherification, and the like. Another suitable class of synthetic engine oils comprises the esters of dicarboxylic acids with a variety of alcohols. Esters useful as synthetic oils also include those made from $C_5$ to $C_{12}$ monocarboxylic acids and polyols and polyol ethers.

Silicon-based oils (such as the polyalkyl-, polyaryl-, polyalkoxy-, or polyaryloxy-siloxane oils and silicate oils) comprise another useful class of synthetic engine oils. Other synthetic engine oils include liquid esters of phosphorus-containing acids, polymeric tetrahydrofurans, poly alpha-olefins, and the like.

In various aspects, the present disclosure provides a method for detecting engine oil degradation by separating an engine oil sample into a polar component and non-polar component. In various aspects, separating comprises extracting the polar component with a polar solvent. In certain aspects, the polar solvent is an alkanol having one to four carbon atoms, such as methanol, ethanol, n-propanol, iso-propanol, and n-butanol, t-butanol, iso-butanol, and the like. In certain aspects, the polar solvent has a polarity index greater than or equal to five. By way of example, a preferred polar solvent comprises methanol ($CH_3OH$), which has a polarity index of about 5.1. A suitable methanol is commercially available at 99.95% purity (e.g., a pesticide grade having trace amounts of any other impurities). Other suitable examples of polar solvents include acetone having a polarity index of about 5.1 and 2-methoxy ethanol having a polarity index of about 5.5. In certain alternate aspects, the polar solvent may include combinations of different compounds, so that the solvent mixture or solution has the desired polarity. For example, in certain alternate embodiments, a mixture of polar solvents may have a polarity index of greater than or equal to 5.

In various aspects, separating further comprises extracting the non-polar component with a non-polar solvent. In various aspects, the non-polar solvent has a polarity index of less than or equal to about one, optionally less than or equal to about 0.5, and in certain aspects equal to about 0.1. In certain aspects, the non-polar solvent is an alkane having six to nine carbon atoms, such as hexane, heptane, octane, or nonane. In certain aspects, the non-polar solvent comprises heptane ($C_7H_{16}$), which has a polarity index of about 0.1. A suitable heptane is commercially available at 99.95% purity (e.g., a pesticide grade having trace amounts of any other impurities). Other suitable non-polar solvents include hexane ($C_6H_{14}$) having a polarity index of about 0.1 and iso-octane also having a polarity index of about 0.1.

As previously discussed, in accordance with the teachings of the present disclosure, the engine oil sample is separated into a polar component and a non-polar component. In various aspects, separating comprises admixing the engine oil sample with a polar solvent to form a first mixture. In other aspects, the engine oil sample is admixed with a non-polar solvent to form a second mixture. A mixture can be a solution of the engine oil sample, the solvent, along with any debris present, so that the admixing of the components is generally a solubilizing process. In certain aspects, the mixture(s) (e.g., solution) is then agitated. The mixture(s) (e.g., solution) can be agitated by shaking, rolling, inverting, sonication or using an automated shaker. In certain aspects, the mixture(s) (e.g., solution) is then agitated. In yet other aspects, the application of heat is avoided to minimize potential evaporation of solvent, thus changing the volume/concentration of the mixture(s) (e.g., solution). In certain aspects, the mixture(s) (e.g., solution) is permitted to settle for separation. While the engine oil sample first mixture settles with a polar solvent, the sample separates into the polar component and non-polar components. While the second mixture with a non-polar solvent separates, the sample likewise separates into polar and non-polar components. By way of example, a 1 ml engine oil sample is mixed with 9 ml of methanol to form a first mixture (e.g., solution) and a 1 ml sample of engine oil is mixed with 9 ml of heptane to form a second mixture (e.g., solution). The first mixture is permitted to settle for at least eighteen hours, optionally about twenty-two hours, in certain aspects preferably twenty-four hours to achieve about 90 to about 95% separation into a polar component and a non-polar component. As appreciated by those of skill in the art, the time permitted for separation may vary depending on the volume of the sample to be separated. In yet other aspects, the non-polar component can also be analyzed; however, the non-polar component (second sample) does not necessarily require such settling and is substantially homogeneous upon immediate agitation, thus it can be analyzed without requiring a settling step (e.g., via gas chromatography/mass spectrometry).

In various aspects, the method of detecting engine oil degradation comprises analyzing the polar component for one or more degradation indicators selected from the group consisting of antioxidants, acid content, and combinations thereof, wherein the degradation indicators relate to a degree of engine oil degradation. Certain degradation indicators of the present disclosure are extracted into the polar phase in accordance with the present teachings. For example, antioxidants are extracted into the polar component. Antioxidants protect against sludge formation. Sludge is formed in engines as the result of a complex degradation of the engine oil. Antioxidants have the ability to neutralize or minimize oil oxidative degradation, but as the engine oil physically wears and chemically ages, the amount of antioxidant present in the engine oil decreases. Thus, the level of one or more antioxidants remaining in an engine oil sample is indicative of the state of degradation of the engine oil during service. In certain aspects, the presence or amount of one or more antioxidants detected provides information regarding the state of oil degradation. While not limiting the present disclosure to any particular theory, where a plurality of antioxidants are included in an engine oil, including phenol-based and amine-based antioxidants, the phenol antioxidants tend to be preferentially consumed to the amine antioxidants, thus providing an additional indication of engine oil degradation. By way of example, a lubricant oil may contain several antioxidants, including those of the phenol and amine chemical families. After a certain period of use, the analyzed engine oil sample may demonstrate that there are no phenol-containing antioxidants remaining and only a few amine-containing antioxidants or none at all, indicating progression of engine oil degradation.

Phenolic antioxidants are well known. Examples of phenolic antioxidants include, but are not limited to: 2,6-di-tertiary-butyl phenol; 2,6-di-tertiary-butyl-4-methyl phenol; tetrakis-[methylene-(3,5-di-tertiary-butyl-4-hydroxyhydrocinnamate)]methane; 1,3,5-tri-methyl-2,4,6-tris-(3,5-di-tertiary-butyl-4-hydroxy-benzyl)benzene; pentaerythrityl tetrakis-[3-(3,5-di-tertiary-butyl4-hydroxy phenyl)propionate]; n-octadecyl-3-(3,5-di-tertiary-butyl-4-hydroxyphenyl) propionate; 4,4'-methylene-bis-(2,6-di-tertiary-butyl-phenol); 4,4'-thio-bis-(6-tertiary-butyl-o-cresol); 2,4-bis-(n-octylthio)-6-(4-hydroxy-phenoxy)-1,3,5-triazine; di-n-octadecyl-3,5-di-tertiary-butyl-4-hydroxybenzyl-phosphonate; 2-(n-octylthio) ethyl-3,5-di-tertiary-butyl-4-hydroxybenzoate; sorbitol hexa-[3-(3,5-di-tertiary-butyl-4-hydroxy phenyl)propionate]; 4,4'-methylenebis[2,6-bis 1,1-dimethylethyl]phenol; and combinations thereof. Examples of amine antioxidants include, but are not limited to: diphenylamine; bis-decylated diphenylamine; octylated diphenylamine; bis-nonyl diphenylamine; nonyl diphenylamine; bis-octylated diphenylamine, decyl diphenylamine; dialkylated diphenylamine, trialkylated diphenylamine, phenyl-alpha-naphthylamine; 4,4'-(1,2 ethenediyl)bis-benzenamine; butylated-octylated diphenylamine; 3-hydroxydiphenylamine, 4-hydroxydiphenylamine, N-phenyl-1,2-phenylenediamine, N-phenyl-1,4-phenylenediamine, mono- and/or di-butyidiphenylamine, mono- and/or di-octyidiphenylamine, mono- and/or di-nonyidiphenylamine, phenyl-α-naphthylamine, phenyl-β-naphthylamine, di-heptyidiphenylamine, mono- and/or di-(α-methylstyryl)diphenylamine, mono- and/or di-styryidiphenylamine, N,N'-diisopropyl-p-phenylenediamine, N,N'-bis(1,4-dimethylpentyl)-p-phenylenediamine, N,N'-bis(1-ethyl-3-methylpentyl)-p-phenylenediamine, N,N'-bis(1-methylheptyl)-p-phenylenediamine, N,N'-diphenyl-p-phenylenediamine, N,N'-di-(naphthyl-2)-p-phenylenediamine, N-isopropyl-N'-phenyl-p-phenylenediamine, N-(1,3-dimethylbutyl)-N'-phenyl-p-phenylenediamine, N-(1-methylpentyl)-N'-phenyl-p-phenylenediamine, N-cyclohexyl-N'-phenyl-p-phenylenediamine, 4-(p-toluenesulfonamido) diphenylamine, 4-isopropoxydiphenylamine, tert-octylated N-phenyl-1-naphthylamino, and mixtures of mono- and dialkylated t-butyl-t-octyidiphenylamines and combinations thereof.

In yet other aspects, the degradation indicator species comprises acid content of the sample, for example, whether the polar component comprises one or more carboxylic acids. As the engine oil physically wears and chemically ages, acid content increases. For example, carboxylic acids contribute to the acidity of the engine oil. The effect of prolonged oxidation is that the engine oil becomes acidic causing corrosion, while an increase in viscosity occurs. In yet other aspects, the acid content degradation indicator species is an acid content level, which represents for example, a level of one or more carboxylic acids. Such acids separate into the polar component, as well during the separation processes of the present disclosure.

The non-polar component comprises a group consisting of heavy carbons, paraffins, zinc, sulfur, phosphorus, wax, combustion by-products, and combinations thereof.

In various aspects, the polar component is analyzed by gas chromatography and then mass spectrometry (GC/MS). Gas chromatography is a method for isolating a sample by its components before it is delivered to a detector for detection. In certain aspects, the interior walls of the gas chromatograph column are coated with a material commonly referred to as a stationary phase. The stationary phase retains the various components of the injected sample and, through the application of heat, releases the components so that they are received by the detector separated in time and is reported in what is called the components retention time. In various aspects, the gas chromatography column is (5%-Phenyl)-methylpolysiloxane.

As is known in the art, heavier components require more heat and/or more time to elute from the column than do lighter components. In various aspects, analyzing comprises heating the polar component to a predetermined temperature during the gas chromatography. By way of example, the polar component is optionally heated to about 75° C. to separate the polar solvent. Thus, in certain aspects, column operation begins at a low temperature of about 75° C. to remove the solvent. Heating up to 200° C. (ramping) isolates or separates any low molecular weight fatty acid methyl esters that may be present in the polar component. In various aspects, the sample in the column is heated to the predetermined temperature, for example, to about 200° C. for about forty-five minutes. While not limiting the present disclosure, exemplary carboxylic acid components generally are separated prior to about 200°, while heating the column to about 200° C. generally separates exemplary phenol antioxidants and some lower molecular weight amine antioxidants. In various aspects, analyzing further comprises heating the polar component to a second predetermined temperature (following the heating to the first predetermined temperature), for example to a second predetermined temperature of about 300° C. for about twenty minutes, optionally for about twenty-two minutes. During the heating, it is generally expected that exemplary higher molecular weight amine antioxidants are separated from the sample at temperatures ranging from 250° C. to 300° C.

In various aspects, the detector for the analysis step is mass spectrometry. In various aspects, analyzing the elute of the polar component comprises the mass spectrum of signal strength data as a function of mass-to-charge ratio. In a mass spectrum, the signal strength data may be in the form of peaks on a chromatogram of signal intensity as a function of mass-to-charge ratio. The intensity of the peak is also generally associated with the apex of the peak. Generally, the mass-to-charge ratio relates to the molecular weight of a potential marker.

In yet other aspects, the detector for the analysis step further comprises Flame Ionization Detector (FID) analysis. The FID provides a series of peaks on the chromatogram and provides a quantitative amount of the species present. In certain aspects, the FID analysis is optionally used along with mass spectrometry analysis, to employ a mass spectra library via the MS that can positively identify the chemical species. Thus, in certain aspects the analysis includes GC/MS and FID of the sample.

In various aspects, the present disclosures provides a method for determining a first amount of one or more degradation indicators selected from the group consisting of antioxidants, acid content, and combinations thereof in a first engine oil composition, by separating the first engine oil composition into a polar component and a non-polar component and analyzing the polar component. The first amount of the one or more degradation indicators relates to a degree of degradation of the first engine oil composition. The method also comprises determining a second amount of one or more degradation indicators selected from the group consisting of antioxidants, acid content, and combinations thereof in a second engine oil composition. The second engine oil composition is distinct from the first engine oil composition. By "distinct," it is meant that the engine oil compositions may be the same formulation, for example, a certain commercially available brand of engine oil, where the first engine oil composition is new and the second engine oil composition has been used in an engine for a specific duration of time. Different oil compositions may also be entirely different engine oils that are compared for relative performance in an internal combustion engine. In certain aspects, an engine oil composition is a new engine oil sample, wherein "new" is defined as a sample that has not been exposed to oxidation, contamination, and/or physical wear in the engine. In certain aspects, an engine oil composition is an old engine oil sample, wherein "old" is defined as a sample that has been exposed to oxidation, contamination, and/or physical wear in the engine.

Thus, the second engine oil composition is separated into a polar component and a non-polar component. The polar component of the second sample is analyzed to determine the second amount of the one or more degradation indicators, which relate to a degree of degradation of the second engine oil composition. The first amount of the one or more degradation indicators from the first engine oil composition is compared to the second amount of the one or more degradation indicators in the second engine oil composition to determine the relative engine oil degradation of the first engine oil composition as compared to the second engine oil composition.

In certain aspects, determining an amount of one or more degradation indicators may simply be detecting the presence or absence of such indicator species. In other aspect, the determining means that the amount of one or more degradation indicators is quantified or semi-quantified. In certain aspects, the amount of one or more degradation indicators is semi-quantified when compared against a calibration curve or a known reference by comparing the integrated peak areas of the indicators and antioxidants. In various aspects, comparing the first amount of the one or more degradation indicators to the second amount of the one or more degradation indicators to semi-quantify the relative engine oil degradation of the first engine oil composition as compared to the second engine oil composition. In embodiments where FID is used for additional analysis, quantification of the chemical compound indicators is also contemplated.

In certain variations, the presence of one or more degradation indicators are compared between a first engine oil composition and a second engine oil composition, which provides general information about the engine oil degradation status. Further, in certain variations, the first and second amounts of one or more degradation indicators are compared with one another to provide additional information about the comparative engine oil degradation status. In other variations, the comparing of the first and second engine oil compositions may include establishing a baseline level for the presence or absence of one or more of the degradation indicator species, which can subsequently be compared with the engine oil during different periods of service to find a rate of engine oil degradation or to further compare engine oil to an established database to determine the status of the sample through service, as compared to typical performance. As can be appreciated by those of skill in the art, the comparison can thus enable testing and optimization of engine performance under different service conditions, as well as informed decisions about appropriate engine oil selection for different engines and operating conditions. This also applies to engine design changes and components. By way of non-limiting example, the techniques of the present disclosure can be used to design the following aspects of engines: whether oil squirters should be added to engines, the design of piston rings, sump depth, positive crankcase ventilation valve (PCV) design, engine exhaust gas recirculation (EGR) design, and oil pump size/speed can be complimented by studying oil degradation levels to help optimize engine operation and reduce the risk of premature wear.

In certain aspects, the present disclosure provides a method for detecting degradation of an engine oil comprising admixing an engine oil sample with both a polar solvent and a non-polar solvent to form a mixture (e.g., solution). The mixture (e.g., solution) is then agitated and permitted to separate for at least twenty-four hours to form a polar component and a non-polar component. The polar solvent comprises an alkanol and the non-polar solvent comprises an alkane. As noted previously, in alternate embodiments where only the non-polar component is to be analyzed, settling is not necessary prior to analysis, as the non-polar component is substantially homogeneous upon agitation. The polar component is then analyzed, for example, by gas chromatography/mass spectrometry (GC/MS), to determine a presence of one or more degradation indicator species selected from the group consisting of antioxidants, acid content, and combinations thereof, which relate to a degree of engine oil degradation, as described previously above.

EXAMPLE 1

In one example, an engine oil sample was provided with 0.25, 0.5% and 1.0% of a pure antioxidant standard to determine appropriate separation time. The samples are all prepared in the same manner by mixing and adding 9 ml of methanol to a 1 ml oil sample, for example. Each respective sample is allowed to settle for a variety of different time intervals (e.g., 12, 18, 24, 48, 72 hours, and 3 weeks). Samples that settled for twenty-four, forty-eight, seventy-two and three weeks each had the same millivolt response on the mass spectrometry MS within the standard error of the MS detector. Thus, adequate separation of about 90-95% based on a five part back to back run is achieved with at least twenty-four hours of separation.

EXAMPLE 2

An engine oil sample is analyzed in Example 2 with GC/MS. 20 ml of pesticide grade heptane (99.95% purity) is poured into a 150 ml beaker and is used to clean glassware. 20 ml of heptane is poured into another 150 ml beaker and covered and 20 ml of methanol is poured into another 150 ml beaker and covered. A 10 ml glass thimble is placed into Wheaton vial rack upside down to dry from rinsing. The engine oil sample is placed in a sample bottle for thirty seconds and shaken from end to end. Then sample bottle is rolled back and forth for thirty seconds. In the alternative, the engine oil sample can be placed on an automated shaker at medium speed and shaken for one minute. Next, the bottom of the sample bottle is checked for any sediment and/or debris. If sediment is present, the sample is shaken until the sediment is gone.

Using a plastic transfer pipette, 1 ml of engine oil is placed into a glass thimble. The plastic transfer pipette is held straight to ensure oil meniscus is level with the 1 ml increment line. Next, 9 ml of methanol is poured into the thimble and the volume is brought up to 10 ml with the solvent meniscus level with the 10 ml increment line. The inversion and shaking is repeated for a total of two minutes. The bottom of thimble is ensured to be free from any oil residue and the mixture appears homogeneous. The solution is poured into an 11 ml scintillation vial, labeled, and placed in Wheaton vial tray upright. In preferred aspects, solvents are handled with glassware, rather than plastics to prevent the leaching of any plasticizers or stabilizers such as phthalates, which may be detected on the chromatogram analysis.

The 11 ml vials are permitted to settle for twenty-four hours in the rack. The oil and methanol solution separates into multiple phases. After the vials have settled for twenty-four hours, a glass transfer Pasteur pipette is used to place 2 ml of the very top layer of the methanol solution into a 2 ml GC vial. Next, the GC vial cap is crimped and placed in GC/MS auto sampler tray. The 11 ml vials are capped and all remaining solutions are refrigerated in storage for up to thirty days. All glassware is triple rinsed, inverted and air dried.

The gas chromatography column type is commercially available from Agilent as DB5MS-HT used in a 6890 Agilent GC gas chromatograph. The mass spectrometer is 5975 MS from Agilent. The column dimensions are 60 m×0.25 mm×0.25 μm. The injection type selected is automatic (AUTO), where the solvent delay is ten min. The inlet temp is 275° C., the transfer temp is 300° C., and the initial oven temperature is 75° C. The initial time hold is at the initial over temperature occurs for about five minutes. A first rate of oven heating (Rate 1) is 2° C./min; a first temperature (Temp 1) is about 200° C. and a hold duration (Hold 1) is about forty-five minutes. A second heating rate (Rate 2) is 5° C./min; where a second predetermined temperature (Temp 2) is 310° C., and a second hold duration (Hold 2) is about 22.5 min. The total run time is 155 min. The mode is pulsed splitless. The gas type is helium. The column flow for the GC analysis is 2 ml/min. The injection volume is 1 μl. The low scan mass is 15 Daltons (Da) and the high scan mass is 900 Da. The EM voltage is 1300-1500 volts depending on autotune. The MS integration parameters for data interpretation initial area reject are 800,000. The initial peak width is 0.15. The shoulder detection is off. The initial threshold is eighteen.

The GC columns are selected to be low bleed columns. A maximum operating temperature is selected to be about 325-330° C., where methylene chloride blanks are run in between every sample for cleaning of the syringe and column. Methylene chloride is used as the wash solvent for the instrument set-up. The high end point temperature elutes the degradation indicator species peaks.

The engine oil is charged into an internal combustion gasoline engine using 5W30 oil, commercially available from ExxonMobil as MobilClean 5W30 having GF-4 quality, as well as other GM factor fill engine oils, are tested in accordance with the preparation and analysis techniques described above (for GC/MS). A sample is taken when the engine oil is new, prior to use in the internal combustion engine. The engine is an LNF 2.0 L 4 cylinder variable valve timing engine which runs a test cycle at seven different speeds and engine loads for various periods of time. The test cycle includes two hot soak times (where the oil is not being aerated and is exposed to heat only). There are also two idle periods, so that the engine oil is pumping and being aerated, but the engine is not under a load. Each mode has monitors for engine oil temperature in the sump, which typically ranges from 60° C. to 120° C. with spikes of 130° C. on occasion during the test. Engine oil can experience degradation (so-called "breaking") of the base oil at 130° C., so this testing provides a thorough challenge for the oil at a wide range of temperatures. The engine is run for a total of twenty-five cycles. Engine oil samples are taken with the new oil, at the start of the test after one cycle, and then at random times near the middle and end of test to monitor the oil condition.

Samples (50 mL each) are taken from the engine oil at thirty hours, 411 hours and 490 hours of use, each of which are respectively tested via GC/MS, as described above FIGS. 1A-D show mass spectrometry analysis following GC of the engine oil (commercially available as a 5W30) tested for degradation indicator species prior to use in an internal combustion engine (0 hours) (FIG. 1A), at thirty hours of use (FIG. 1B), at 411 hours of use (FIG. 1C), and at 490hours of use (FIG. 1D). It should be appreciated that these trials vary depending upon when the sample is taken during the engine oil testing run. As can be seen from the figures, degradation indicator species, namely, combustion products and carboxylic acids begin to form in the engine oil sample in FIG. 1C after 411 hours of use in the engine; in FIG. 1D, it can be observed that the degradation indicator, antioxidants, are depleting, while the combustion products and carboxylic acids are increasing, thus showing degradation of the engine oil.

What is claimed is:

1. A method for detecting degradation of an engine oil comprising:
    separating an engine oil sample into a polar component and a non-polar component; and
    analyzing the polar component for one or more degradation indicators selected from the group consisting of antioxidants, acid content, and combinations thereof, wherein said degradation indicators relate to a degree of engine oil degradation.

2. The method according to claim 1, wherein said separating comprises extracting said polar component with a polar solvent having a polarity index greater than or equal to five.

3. The method according to claim 2, wherein said polar solvent comprises methanol.

4. The method according to claim 1, wherein said separating comprises extracting said non-polar component with a non-polar solvent having a polarity index of less than or equal to about one.

5. The method according to claim 4, wherein said non-polar solvent comprises heptane.

6. The method according to claim 1, wherein said separating further comprises admixing said engine oil sample with said polar solvent to form a first mixture; agitating said first mixture; and permitting said first mixture to settle for at least twenty-four hours.

7. The method according to claim 6, wherein said admixing further comprises mixing said engine oil sample with a non-polar solvent and said polar solvent to form said first mixture.

8. The method according to claim 1, wherein said analyzing of said polar component is conducted by gas chromatography and mass spectrometry (GC/MS).

9. The method according to claim 8, wherein a gas chromatography column used during said gas chromatography (GC) comprises 5%-phenyl-95% dimethylpolysiloxane.

10. The method according to claim 8, wherein said analyzing comprises heating said polar component to a predetermined temperature of about 200° C. during said gas chromatography.

11. The method according to claim 10, wherein said analyzing further comprises heating said engine oil sample to a second predetermined temperature of about 300° C. after said predetermined temperature.

12. The method according to claim 8, wherein said analyzing of said polar component further comprises Flame Ionization Detection (FID) after said gas chromatography and mass spectrometry (GC/MS).

13. The method according to claim 1, wherein said one or more degradation indicators is selected from the group consisting of 2,6-di-tertiary-butyl phenol, 2,6-di-tert-butyl-4-methylphenol, diphenylamine, phenyl-alpha-naphthylamine, 4,4'-(1,2 ethenediyl) bis-benzenamine, butylated-octylated diphenylamine, 4,4'-methylenebis [2,6-bis 1,1-dimethylethyl] phenol, octylated diphenylamine, bis-nonyl diphenylamine, and combinations thereof.

14. The method according to claim 1, wherein said one or more degradation indicators comprises one or more carboxylic acids.

15. A method for detecting engine oil degradation comprising:
   determining a first amount of one or more degradation indicators selected from the group consisting of antioxidants, acid content, and combinations thereof in a first engine oil composition, by separating said first engine oil composition into a polar component and a non-polar component and analyzing said polar component, wherein said first amount of said one or more degradation indicators relates to a degree of degradation of said first engine oil composition;
   determining a second amount of one or more degradation indicators selected from the group consisting of antioxidants, acid content, and combinations thereof in a second engine oil composition that is distinct from said first engine oil composition, by separating said second engine oil composition into a polar component and a non-polar component and analyzing said polar component, wherein said second amount of said one or more degradation indicators relates to a degree of degradation of said second engine oil composition; and
   comparing said first amount of said one or more degradation indicators to said second amount of said one or more degradation indicators to determine the relative engine oil degradation of said first oil composition as compared to said second oil composition.

16. The method according to claim 15, wherein said separating said first engine oil composition comprises admixing said first engine oil composition with both a non-polar solvent comprising heptane and said polar solvent comprising methanol so as to extract said polar component with said polar solvent comprising methanol from said first engine oil composition, and said non-polar component with said non-polar solvent comprising heptane from said first engine oil composition, and said separating said second engine oil composition further comprises admixing said second engine oil composition with both said non-polar solvent comprising heptane and said polar solvent comprising methanol so as to extract said polar component from said second engine oil composition with said polar solvent and said non-polar component with said non-polar solvent from said second engine oil composition.

17. The method according to claim 16, wherein said separating further comprises admixing said first engine oil composition with said polar solvent and said non-polar solvent to form a first mixture; agitating said first mixture; and
   permitting said first mixture to settle for at least twenty-four hours and said separating of said second engine oil composition further comprises admixing said second engine oil composition with said polar solvent and said non-polar solvent to form a second mixture; agitating said second mixture; and permitting said second mixture to settle for at least twenty-four hours.

18. The method according to claim 15, wherein said determining comprises analyzing said first engine oil composition polar component and said second engine oil composition polar component separately by gas chromatography and mass spectrometry (GC/MS), wherein a GC column of said GC/MS comprises 5%-phenyl-95% dimethylpolysiloxane.

19. The method according to claim 15, wherein said one or more degradation indicators is selected from the group consisting of 2,6-di-tertiary-butyl phenol, 2,6-di-tert-butyl-4-methylphenol, diphenylamine, phenyl-alpha-naphthylamine, 4,4'-(1,2 ethenediyl) bis-benzenamine, butylated-octylated diphenylamine, 4,4'-methylenebis [2,6-bis 1,1-dimethylethyl] phenol, octylated diphenylamine, bis-nonyl diphenylamine, carboxylic acids, and combinations thereof.

20. A method for detecting degradation of an engine oil comprising:
   admixing an engine oil sample with a polar solvent comprising alkanol to form a mixture; agitating said mixture; and permitting said mixture to separate for at least twenty-four hours to form a polar component and a non-polar component; and
   analyzing said polar component by gas chromatography/mass spectrometry (GC/MS) to determine a presence of one or more degradation indicator species selected from the group consisting of antioxidants, acid content, and combinations thereof, which relate to a degree of engine oil degradation.

21. The method according to claim 20, wherein said gas chromatography (GC) employs a column comprising 5%-phenyl-95% dimethylpolysiloxane.

22. The method according to claim 20, wherein said antioxidant degradation indicator species is selected from the group consisting of 2,6-di-tertiary-butyl phenol, 2,6-di-tert-butyl-4-methylphenol, diphenylamine, phenyl-alpha-naphthylamine, 4,4'-(1,2 ethenediyl) bis-benzenamine, butylated-octylated diphenylamine, 4,4'-methylenebis [2,6-bis 1,1-dimethylethyl] phenol, octylated diphenylamine, bis-nonyl diphenylamine, carboxylic acids, and combinations thereof.

* * * * *